(12) United States Patent
Wright

(10) Patent No.: US 9,155,604 B1
(45) Date of Patent: Oct. 13, 2015

(54) EXTRAOCULAR MUSCLE SUPPORT SLING

(71) Applicant: Kenneth W. Wright, Los Angeles, CA (US)

(72) Inventor: Kenneth W. Wright, Los Angeles, CA (US)

(*) Notice: Subject to any disclaimer, the term of this patent is extended or adjusted under 35 U.S.C. 154(b) by 257 days.

(21) Appl. No.: 13/752,637

(22) Filed: Jan. 29, 2013

(51) Int. Cl.
*A61F 2/14* (2006.01)
*A61F 2/00* (2006.01)

(52) U.S. Cl.
CPC .................... *A61F 2/0063* (2013.01)

(58) Field of Classification Search
CPC .... A61F 2/0045; A61F 9/00718; A61N 25/02
USPC ............ 600/37; 128/897–899; 623/4.1
See application file for complete search history.

(56) References Cited

U.S. PATENT DOCUMENTS

2004/0254420 A1* 12/2004 Ward .................... 600/37

* cited by examiner

*Primary Examiner* — Christine H Matthews
*Assistant Examiner* — Joshua D Lannu
(74) *Attorney, Agent, or Firm* — Morland C. Fischer

(57) ABSTRACT

An extraocular muscle support sling and a method for surgically implanting the sling to reinforce a weak or ineffective extraocular muscle. The sling includes a semi-flexible anchor base and a pair of elastic arms which extend from the anchor base and are held together to create a loop. During implantation, the anchor base of the sling is attached to a movable target tissue of the patient, and the looped elastic arms are attached to an immobile base tissue. A pulling or tensioned force applied to the elastic arms causes the patient's movable target tissue to which the anchor base is attached to be pulled towards and oriented with respect to the immobile base tissue with the same force and in the same direction as would be the case had the muscle been normal. According to preferred embodiments, the extraocular muscle support sling has particular application for treating ptosis and strabismus.

20 Claims, 4 Drawing Sheets

EXTRAOCULAR MUSCLE SUPPORT SLING

BACKGROUND OF THE INVENTION

1. Field of the Invention

This invention relates to an implantable surgical muscle support sling to reinforce a weak or ineffective extraocular muscle for ideally treating ptosis and strabismus. The muscle support sling is sutured between a movable target (i.e., insertion) tissue and an immobile base (i.e., origin) tissue to orient and hold the target tissue relative to the base tissue as would have been the case had the extraocular muscle been normal.

2. Background Art

It is sometimes necessary to overcome the effects of a weak or ineffective ocular muscle which is known to cause ptosis or strabismus. To treat these problems, a movable target tissue of a patient is repositioned relative to an immobile base tissue to correspondingly reposition the patient's eyelid or realign the patient's eyeball. Repositioning the eyelid to treat ptosis is typically accomplished by one or more thin threads which are sutured between the target and base tissues. However, the conventional threads tend to migrate or "cheese wire" through the patient's tissues over time. Consequently, the patient's eyelid will droop once again or the eyeball becomes misaligned so that the original problem recurs in a few months. What is more, using the conventional threads to treat ptosis often causes unsightly peaking or notching of the eyelid when the patient's target tissue below the eyelid is pulled towards the base tissue near the eyebrow. In this same regard, no elastic thread implant system is readily available that effectively repositions the eyeball to treat strabismus. Accordingly, a more effective and cosmetically acceptable means and procedure for treating ptosis and strabismus are desirable.

SUMMARY OF THE INVENTION

In general terms, disclosed are an extraocular muscle support sling and a method by which the sling is implanted during a surgical procedure for treating ptosis (i.e., droopy eyelid) and paralytic strabismus (i.e., misalignment of the eyeball because of a weak or ineffective muscle). The extraocular muscle support sling functions as an artificial ocular muscle to reinforce a weak or ineffective normal muscle. The sling includes a semi-flexible anchor base having a set of anchoring holes formed therethrough to receive sutures by which to affix the anchor base to a movable target tissue of a patient. A pair of elongated elastic arms are attached at first ends thereof to respective ends of the anchor base. By applying a tension or pulling force on the pair of arms, the target tissue of the patient to which the anchor base is affixed can be correspondingly displaced relative to an immobile base tissue.

An elastic sleeve surrounds the opposite free ends of the arms by which to hold the arms tightly against one another such that the arms form a loop between the anchor base and the sleeve. During implantation of the muscle support sling, the anchor base is attached to the patient's movable target tissue, and the sleeve which holds the elastic arms together is attached to the patient's immobile base tissue. The looped elastic arms are woven through the tissue lying between the target and base tissues. The tension in the arms and the pulling force applied to the anchor base is selectively adjusted by increasing or decreasing the size of the loop between the anchor base and the sleeve. The muscle support sling replicates the function of a normal muscle by pulling the patient's movable target tissue towards the immobile base tissue.

By way of a first example, the extraocular sling is used to treat ptosis, where the patient's eyelid is pulled upwardly towards the eyebrow. In this case, the anchor base is sutured to the tarsus of the upper eyelid, and the elastic arms are sutured to the deep tissue above the eyebrow. By way of another example, the extraocular sling is used to treat strabismus, where the patient's eyeball is pulled back into a normal alignment. In this case, the anchor base is sutured to the sclera below a weak lateral rectus muscle and the tendon insertion thereof, and the loop formed by the elastic arms are sutured to the periosteum of the orbital wall posterior and in line with the weak muscle insertion.

DESCRIPTION OF THE PREFERRED EMBODIMENT

Figure 1:
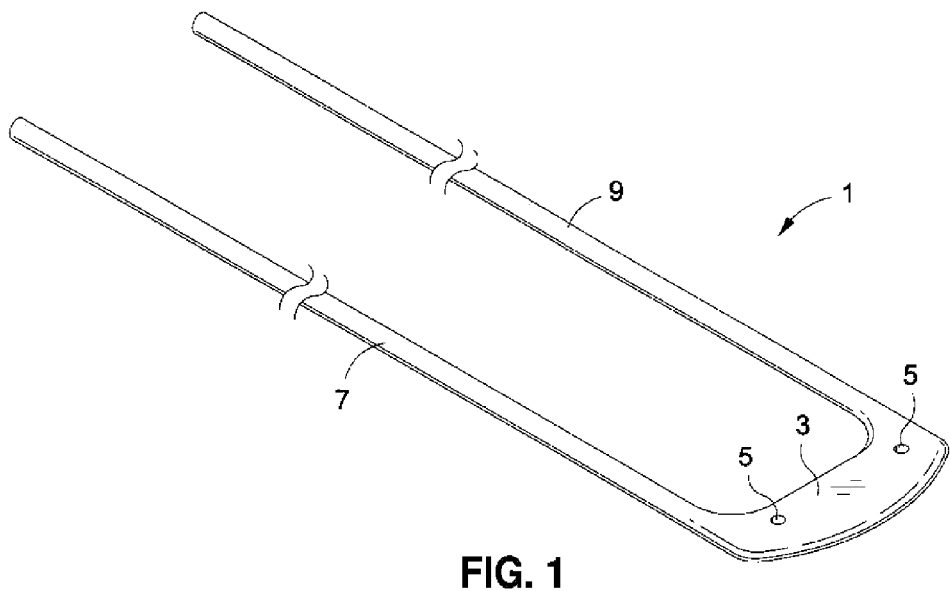
FIG. 1 is a perspective view of an extraocular muscle support sling including an anchor base and a pair of elastic arms according to a preferred embodiment of this invention.
Figure 2:
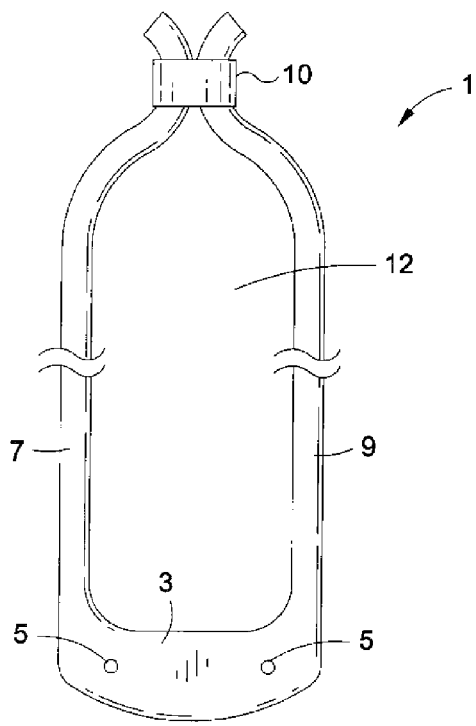
FIG. 2 is a top plan view of the extraocular muscle support sling of FIG. 1.

Referring initially to FIGS. 1 and 2 of the drawings, there is shown an extraocular muscle support sling 1 which in its preferred embodiment is an implantable surgical device having particular application for treating ptosis (sometimes referred to as droopy eyelid) and strabismus (an eye misalignment typically caused by a weak or ineffective rectus muscle). As will be described in greater detail hereinafter, the extraocular muscle support sling 1 functions as an artificial muscle to orient and hold a patient's tissue by active contraction or passive elasticity so as to overcome the effects of a weak or ineffective natural muscle.

The extraocular muscle support sling 1 includes a semi-flexible anchor base 3. The anchor base plate 3 is preferably manufactured from a surgical grade flexible biocompatible material, such as a medical grade silicone. By way of example only, the anchor base 3 has an ideal length of about 8.0 mm and a width of about 3.5 mm. A set of (e.g., two) anchoring holes 5 are formed through anchor base 3.

Figure 6:
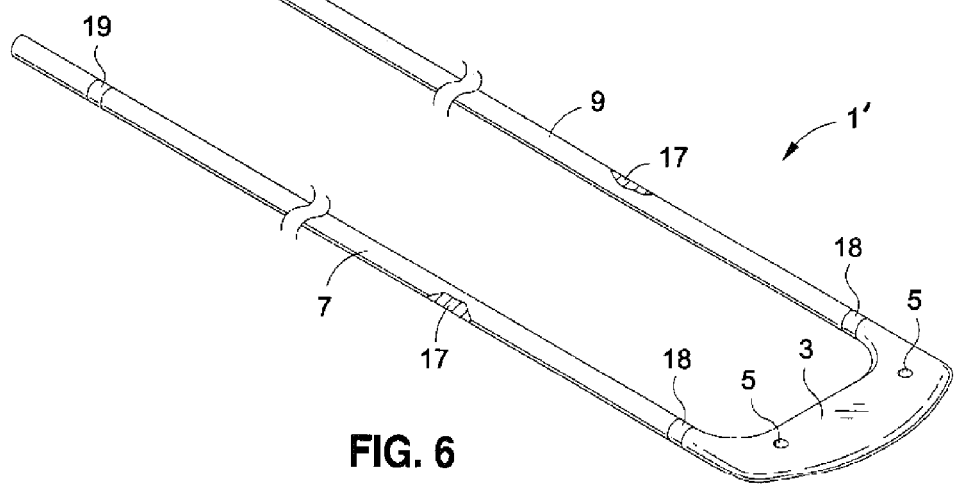
FIG. 6 shows an alternate embodiment of the extraocular muscle support sling of FIG. 1.

First ends of a pair of narrow, elongated arms 7 and 9 are coextensive to respective ends of the anchor base 3. The elongated arms 7 and 9 are preferably manufactured from a surgical grade flexible and elastic biocompatible material, such as medical grade silicon or any other elastic or spring materials that provide elasticity and passive contractility. Moreover, it is within the scope of this invention to manufacture the sling arms 7 and 9 of a modified muscle support sling (designated 1' in FIG. 6) from an electrically-conductive contractile piezoelectric material 17 that can receive an electrical stimulation. To this end, electrical terminals 18 and 19 can be formed at opposite ends of each of the sling arms 7 and 9 to receive an electrical potential and thereby generate a small current flow to cause the sling arms to contract and change their shape to actively move the anchor base plate 3 to which the sling arms 7 and 9 are connected. In the case of treating ptosis in a manner that will soon be described, providing the electrically-conductive sling arms 7 and 9 with an electrical stimulation can actively elevate the patient's eyelid.

When the muscle support sling 1 is implanted, the anchor base 3 is affixed to a patient's target (i.e., insertion) tissue that is movable in response to a tension or pulling force applied thereto, and the pair of elastic arms 7 and 9 that extend from the anchor base 3 are affixed to an immobile base (i.e., origin) tissue of the patient. The free ends of the elastic arms 7 and 9 are surrounded by and held tightly against one another by means of an elastic sleeve 10 so that the arms form a loop 12 between the anchor base 3 and the sleeve 10. However, rather than using the sleeve 10 to create the loop 12, the free ends of the arms 7 and 9 can be tied together in a knot or lashed to one another by a suture. Any excess length may be simply cut off the free ends of the arms.

During implantation of the muscle support sling 1, the flexible elastic arms 7 and 9 which create the loop 12 are attached to the patient's tissue by means of weaving the arms through and/or suturing the arms to the immobile base tissue. The anchor base 3 from which the arms 7 and 9 depend is fixed to the patient's movable target tissue by means of sutures which run through the set of anchoring holes 5 in the anchor base 3.

Figure 3:
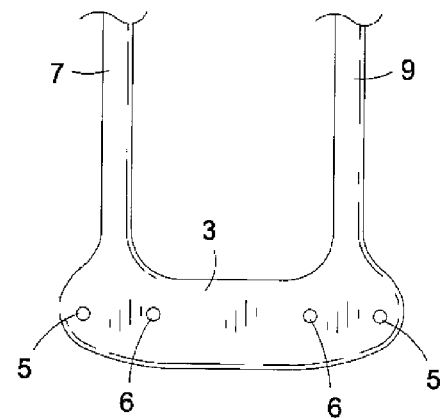
FIG. 3 shows a modified anchor base for the extraocular muscle support sling of FIGS. 1 and 2.

Referring briefly to FIG. 3, the anchor base 3 of the muscle support sling 1 is shown having pairs of anchor holes 5 and 6 located through each end thereof. The additional anchor holes 6 relative to those shown in FIGS. 1 and 2 provide greater stability and a more reliable implant when the anchor base 3 is attached to the target tissue.

The tension generated by the extraocular muscle support sling 1 is selectively adjusted by pulling on or relaxing the elastic arms 7 and 9 to either reduce or increase the size of the loop 12 between the anchor base 3 and the elastic sleeve 10. That is, when the size of the loop 12 is reduced, the tension on the muscle support sling 1 and the pulling force applied to the anchor base 3 will be increased, and when the size of the loop 12 is increased, the tension on the sling and the pulling force applied to the anchor base 3 will be reduced. The muscle support sling 1 is adapted to pull the patient's target towards the base tissue depending upon the tension in the arms 7 and 9 of the sling. The pulling force generated by the muscle support sling 1 replicates the function of a normal muscle pulling the target tissue towards the base tissue. In other words, the sling 1 is implanted and oriented so as to pull the target tissue with the same force and in the same direction as would a normal muscle to thereby reinforce the action of a weak, damaged or ineffective muscle.

Figure 4:
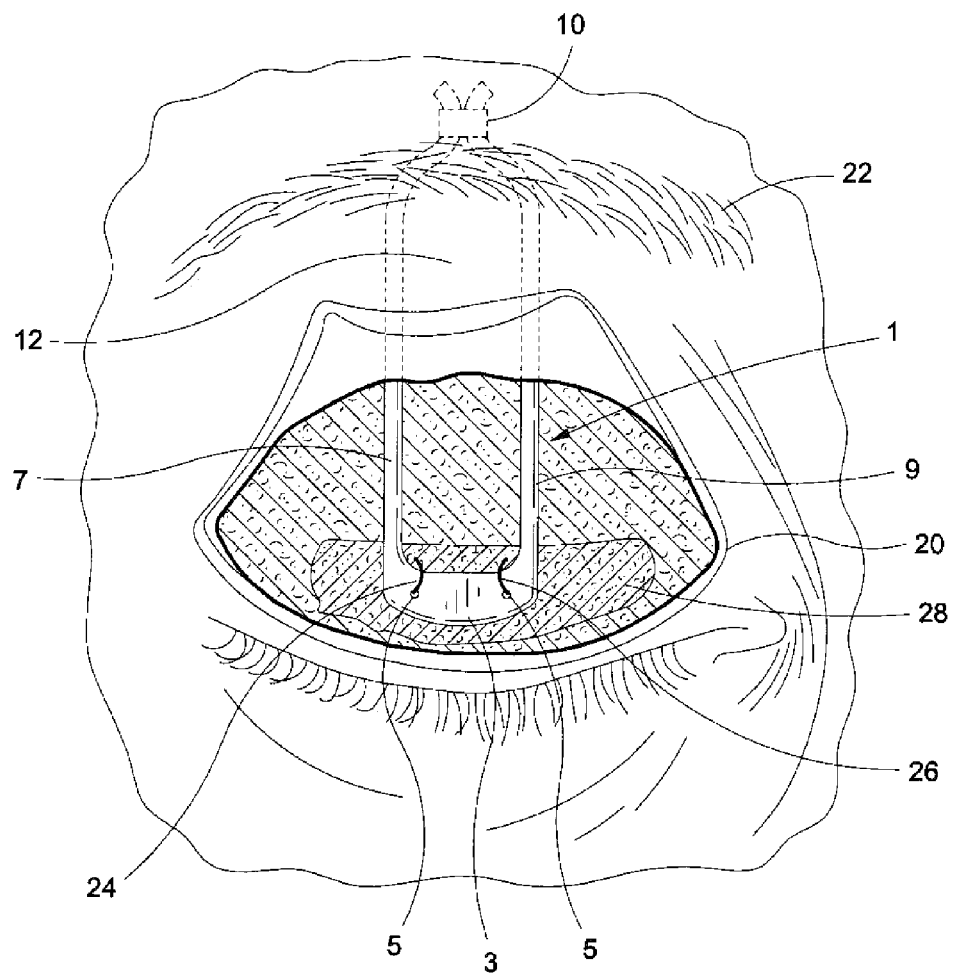
FIGS. 4 and 4A are illustrative of two examples where the extraocular sling is implanted to treat a patient for ptosis.
Figure 4A:
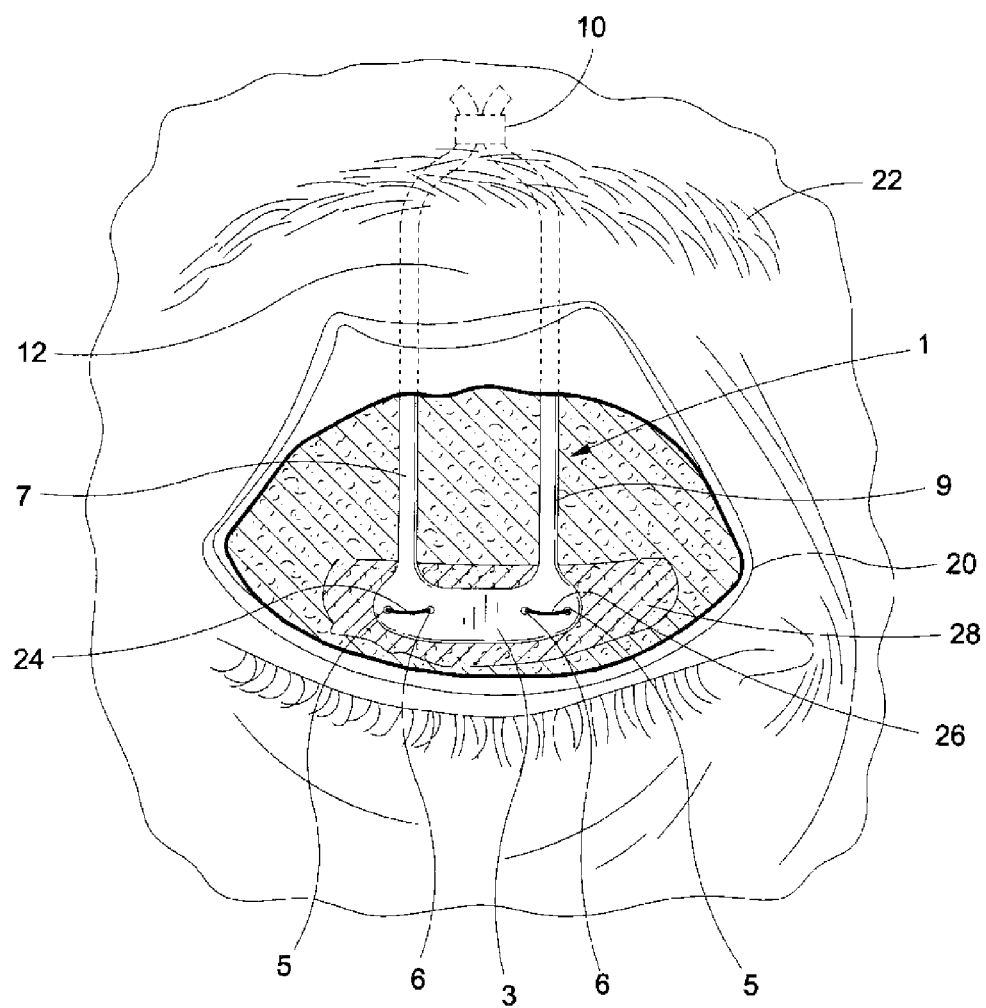

Referring in this regard to FIGS. 4 and 4A of the drawings, the extraocular muscle support sling 1 of FIGS. 1-3 is shown being used to treat a patient for ptosis by pulling the eyelid 20 upwardly towards the eyebrow 22. In the case of treating ptosis, the anchor base 3 of the muscle support sling 1 is fixed by means of sutures 24 and 26 through the anchoring holes (designated 5 in FIGS. 4 and 5, 6 in FIG. 4A) to the tarsus 28 of the upper eyelid 20 which becomes the movable target tissue. The free ends of the elastic arms 7 and 9 that are held tightly together by the elastic sleeve 10 are drawn through the deep tissue under the eyebrow 22 to be sutured to the tissue above the eyebrow (which may include the periosteum) which is the immobile base tissue. In particular, the loop 12 of the muscle sling support 1 may be woven directly into the sub-brow tissue by means of an islet tipped needle or needles or the like (not shown) attached to the free ends of the arms 7 and 9.

The anchor base 3 of the muscle support sling 1 is attached to the lower aspect of the patient's eyelid 20 by suturing to the tarsus 28 close to the eyelid margin. Because the tarsus 28 in the eyelid is firm tissue, the anchor base 3 will be reliably fixed in place so as to be capable of transferring a pulling force applied thereto to the eyelid. The looped pair of arms 7 and 9 which extend from respective ends of the anchor base 3 are then fed upwardly underneath the skin below the eyebrow 22 to be attached above the eyebrow as previously explained. The arms 7 and 9 are pulled taut or made lax (i.e., relaxed) relative to the sleeve 10 to correspondingly change the size of the loop 12 and thereby raise or lower the patient's upper eyelid 20 so that the position of the eyelid is selectively adjusted as is necessary to correct the ptosis.

Applying a pulling force to the anchor base 3 by tensioning the elastic arms 7 and 9 provides the advantage of distributing the pulling force over the entire surface area of the anchor base 3. This feature helps to reduce eyelid notching and peaking of the lid margin resulting in a more aesthetically pleasing cosmetic appearance than had only a pair of threads been used to treat the ptosis as is common to conventional treatment procedures. What is more, including the anchor base 3 in combination with the elastic arms 7 and 9 contributes to an even elevation of the patient's eyelid to create a smooth eyelid contour.

Figure 5:
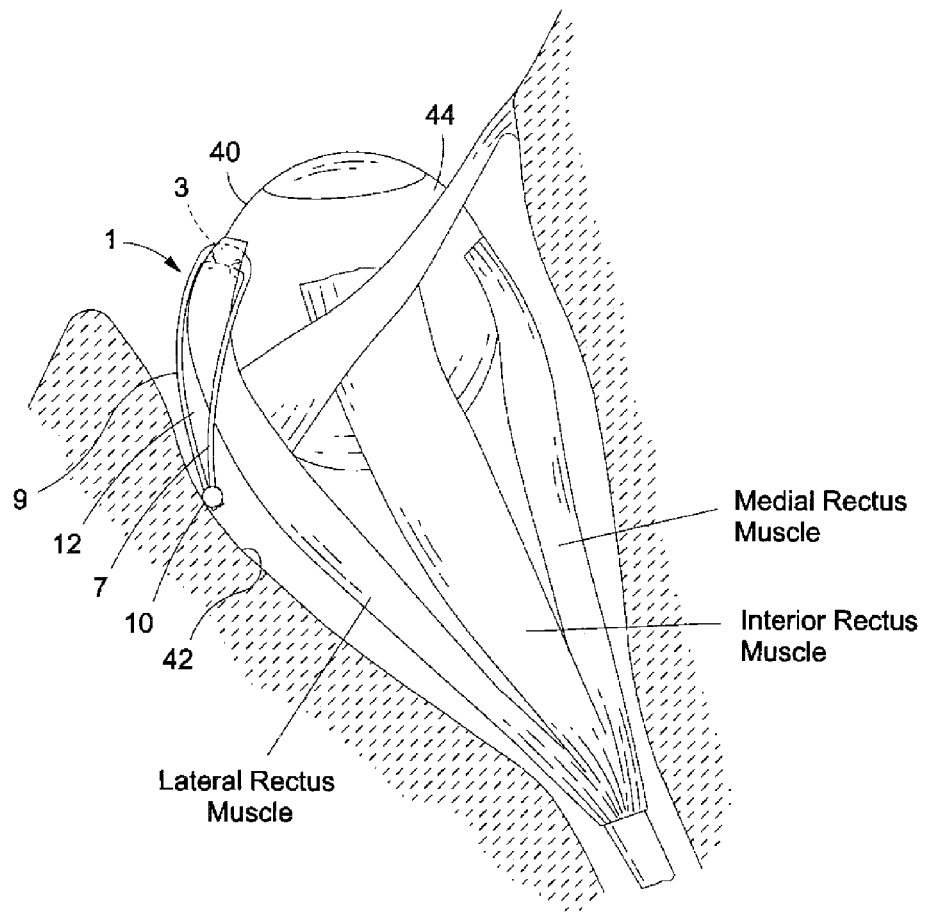
FIG. 5 is illustrative of another example where the extraocular sling is implanted to treat paralytic strabismus.

Turning now to FIG. 5 of the drawings, the extraocular muscle support sling 1 of FIGS. 1 and 2 is shown being used to treat a patient for paralytic strabismus (i.e., eye misalignment) caused by an extraocular muscle palsy (e.g., a stroke) or an ineffective muscle. Paralytic strabismus can occur as a result of muscle damage or as a consequence of the muscle being detached from its insertion on the eye or from lack of appropriate nerve inervation. While the support sling 1 can be used for any weak extraocular muscle, in the particular case of treating a weak lateral rectus muscle, the anchor base 3 of the muscle support sling 1 is located below the lateral rectus muscle and sutured to the patient's sclera (eye wall) 40 and tendon insertion. The elastic arms 7 and 9 which are received through and held together by the sleeve 10 are anchored (i.e., sutured) to the periosteum of the orbital wall posterior 42 behind the insertion of the weak lateral rectus muscle.

A pulling force is applied to the anchor base 3 of the muscle support sling by applying a corresponding pulling force on each of the elastic arms 7 and 9 to adjust the size of the loop 12 and thereby tighten the arms 7 and 9 between the base 3 and the sleeve 10. Holding the arms 7 and 9 under tension and pulling on the anchor base 3 causes the patient's eyeball 44 to rotate in the direction of and along the axis of action of the weak lateral rectus muscle. By virtue of the foregoing, the patient's eyeball 44 is pulled into a proper alignment as would be the case had the lateral rectus muscle been functioning normally so that the patient's strabismus will be corrected.

By way of a particular example, and continuing to refer to FIG. 5, the extraocular muscle support sling 1 can ideally be used to treat a lateral rectus palsy known to cause esotropia. In this case, the anchor base 3 of the muscle support sling 1 is secured by means of suturing through the anchoring holes 5 thereof under the paretic lateral rectus muscle insertion to the patient's sclera 40 and tendon insertion. The looped elastic arms 7 and 9 which depend from respective ends of the anchor base 3 are sutured to the posterior nasal wall periosteum closer to the lateral rectus origin. The elastic arms 9 and 10 are then pulled through or loosened from the elastic sleeve 10 until the patient's eyeball 44 is moved to its normal alignment as if the palsy had not occurred.

The intraocular muscle support sling 1 of this invention including the anchor base 3 and the anchoring holes 5 and 6 (of FIG. 3) therethrough enable suturing the base 3 to the tarsus of the eyelid to correct ptosis as illustrated in FIG. 4 or to the sclera to correct stabismus as illustrated in FIG. 5. Thus, the muscle support sling 1 will be reliably held in place during the healing process to create a stronger implant and a larger area to which the patient's tissue can bond than had a pair of threads been solely used for treatment. In particular, the patient's tissue can grow through the anchoring holes 5 and 6 to produce tissue rivets or anchors and thereby prevent an unintended migration of the anchor base 3.

The invention claimed is:

1. A surgical method for attaching an extraocular muscle support sling to a patient to reinforce a weak or ineffective normal extraocular muscle of the patient, wherein said sling includes an anchor base and a pair of flexible elastic arms attached at first ends thereof to respective ends of the anchor base so that opposite free ends of the pair of flexible elastic arms extend outwardly from said anchor base, and wherein the pair of flexible elastic arms are manufactured from a contractile electrically-conductive material, said method comprising the steps of:
attaching said anchor base to a movable target tissue adjacent an eye of a patient;
exerting a pulling force on the opposite free ends of the pair of flexible elastic arms so that the anchor base and the movable target tissue to which the anchor base is attached are pulled towards an immobile base tissue adjacent the eye of the patient;
attaching the opposite free ends of the pair of flexible elastic arms to the immobile base tissue; and
providing an electrical stimulus to each of said contractile electrically-conductive arms to cause a current to flow through said arms and said arms to contract to correspondingly generate said pulling force for pulling said anchor base towards the patients immobile base tissue.

2. The surgical method recited in claim 1, comprising the additional step of attaching the anchor base of said extraocular muscle support sling to the patient's movable target tissue by means of suturing.

3. The surgical method recited in claim 2, wherein the anchor base of said extraocular muscle support sling has a set of anchoring holes formed therethrough, said method comprising the additional step of suturing the anchor base to the patient's movable target tissue by way of the anchoring holes through said anchor base.

4. The surgical method recited in claim 1, comprising the additional steps of holding the opposite free ends of said pair of flexible elastic arms which extend outwardly from the anchor base of said extraocular muscle support sling together such that said opposite free ends form a loop; and attaching the loop formed by said free ends to the immobile base tissue of the patient.

5. The surgical method recited in claim 1, wherein said extraocular muscle support sling also includes a hollow sleeve, said method comprising the additional steps of feeding the opposite free ends of said pair of flexible elastic arms which extend outwardly from the anchor base of said sling through said hollow sleeve, whereby said opposite free ends are held one against the other in order to form a loop having a size; and attaching the loop formed by said opposite free ends to the immobile base tissue of the patient.

6. The surgical method recited in claim 5, comprising the additional step of pulling the opposite free ends of said pair of flexible elastic arms through said hollow sleeve for correspondingly adjusting the size of said loop and the pulling force exerted on said opposite free ends and applied to the anchor base.

7. The surgical method recited in claim 1, comprising the additional steps of treating the patient for ptosis by attaching the anchor base of said extraocular muscle support sling to a tarsus of an upper eyelid of the patient and attaching the opposite free ends of the pair of flexible elastic arms which extend outwardly from said anchor base to tissue under the eyebrow of the patient.

8. The surgical method recited in claim 7, comprising the additional step of weaving the opposite free ends of said pair of flexible elastic arms into the subbrow tissue of the patient.

9. The surgical method recited in claim 1, comprising the additional steps of treating the patient for strabismus by attaching the anchor base of said extraocular muscle support sling to the patient's sclera and attaching the opposite free ends of the pair of flexible elastic arms which extend outwardly from said anchor base to a periosteum of an orbital wall of the eye of the patient.

10. The surgical method recited in claim 1, comprising the additional steps of forming electrical terminals at the opposite free ends of each of said pair of contractile electrically-conductive flexible elastic arms and providing said electrical stimulus across said electrical terminals to cause the current to flow through said flexible elastic arms.

11. A method for surgically attaching an extraocular muscle support sling to a patient to treat the patient for ptosis, wherein said sling includes an anchor base and a pair of arms attached at first ends thereof to respective ends of the anchor base so that opposite free ends of the pair of arms extend outwardly from said anchor base, said method comprising the steps of:
attaching the anchor base of the extraocular muscle support sling to the tarsus of an eyelid of the patient;
exerting a pulling force on the opposite free ends of the pair of arms of the extraocular muscle support sling so that the anchor base and the patient's eyelid to which the anchor base is attached are pulled towards the eyebrow above the eyelid of the patient; and
attaching the opposite free ends of the pair of arms to tissue under the eyebrow of the patient towards which the anchor base and the patients eyelid are pulled.

12. The method recited in claim 11, comprising the additional step of weaving the opposite free ends of said pair of arms into subbrow tissue of the patient which lies under the eyebrow of the patient towards which the anchor base and the patient's eyelid are pulled.

13. The method recited in claim 11, comprising the additional steps of holding the opposite free ends of said pair of arms which extend outwardly from the anchor base of said extraocular muscle support sling together such that said free ends form a loop; and attaching the loop formed by said opposite free ends to the tissue under the eyebrow of the patient.

14. The method recited in claim 11, wherein said extraocular muscle support sling also includes a hollow sleeve, said method comprising the additional steps of feeding the opposite free ends of said pair of arms which extend outwardly from the anchor base of said sling through said hollow sleeve, whereby said opposite free ends are held one against the other in order to form a loop having a size; and attaching the loop formed by said opposite free ends to the tissue under the eyebrow of the patient.

15. The method recited in claim 14, comprising the additional step of pulling the opposite free ends of said pair of arms through said hollow sleeve for correspondingly adjusting both the size of said loop and the pulling force exerted on said opposite free ends and applied to the anchor base.

16. A method for surgically attaching an extraocular muscle support sling to a patient to treat the patient for strabismus, wherein said sling includes an anchor base and a pair of arms attached at first ends thereof to respective ends of the anchor base so that opposite free ends of the pair of arms extend outwardly from said anchor base, said method comprising the steps of:
- attaching the anchor base of the extraocular muscle support sling to the patients sclera;
- exerting a pulling force on the opposite free ends of the pair of arms of the extraocular muscle support sling so that anchor base and the sclera to which the anchor base is attached are pulled towards an orbital wall of an eye of the patient; and
- attaching the opposite free ends of the pair of arms to the periosteum of the orbital wall of the eye of the patient.

17. The method recited in claim 16, comprising the additional steps of holding the opposite free ends of said pair of arms which extend outwardly from the anchor base of said extraocular muscle support sling together such that said opposite free ends form a loop; and attaching the loop formed by said opposite free ends to the periosteum of the orbital wall of the patient's eye.

18. The method recited in claim 16, wherein said extraocular muscle support sling also includes a hollow sleeve, said method comprising the additional steps of feeding the opposite free ends of said pair of arms which extend outwardly from the anchor base of said sling through said hollow sleeve, whereby said opposite free ends are held one against the other in order to form a loop having a size; and attaching the loop formed by said opposite free ends to the periosteum of the orbital wall of the patient's eye.

19. The method recited in claim 18, comprising the additional step of pulling the opposite free ends of said pair of arms through said hollow sleeve for correspondingly adjusting both the size of said loop and the pulling force exerted on said opposite free ends and applied to the anchor base.

20. The method recited in claim 16, wherein each of the pair of arms attached to the anchor base of the extraocular muscle support sling is manufactured from a flexible elastic material.

* * * * *